US010299903B2

(12) United States Patent
Buckley et al.

(10) Patent No.: US 10,299,903 B2
(45) Date of Patent: *May 28, 2019

(54) FLUID DISPENSER

(71) Applicant: Te Pari Products Limited, North Otago (NZ)

(72) Inventors: Paul Fleming Buckley, Auckland (NZ); Malcolm Lynd, Auckland (NZ)

(73) Assignee: Te Pari Products Limited, Oamaru (NZ)

(*) Notice: Subject to any disclaimer, the term of this patent is extended or adjusted under 35 U.S.C. 154(b) by 331 days.

This patent is subject to a terminal disclaimer.

(21) Appl. No.: 15/100,998

(22) PCT Filed: Jan. 27, 2015

(86) PCT No.: PCT/NZ2015/000005
§ 371 (c)(1),
(2) Date: Jun. 2, 2016

(87) PCT Pub. No.: WO2015/112027
PCT Pub. Date: Jul. 30, 2015

(65) Prior Publication Data
US 2016/0296313 A1    Oct. 13, 2016

(30) Foreign Application Priority Data

Jan. 27, 2014  (NZ) ........................... 631439
Aug. 4, 2014   (NZ) ........................... 628257
(Continued)

(51) Int. Cl.
A61D 7/00      (2006.01)
A61J 7/00      (2006.01)
(Continued)

(52) U.S. Cl.
CPC .............. *A61D 7/00* (2013.01); *A61J 7/0053* (2013.01); *A61M 5/1452* (2013.01);
(Continued)

(58) Field of Classification Search
CPC ................ A61M 5/1452; A61M 5/204; A61M 2250/00; A61M 2005/31588; A61D 7/00; A61J 7/0053
See application file for complete search history.

(56) References Cited

U.S. PATENT DOCUMENTS 3,051,173 A    8/1962   Johnson et al.
3,353,537 A   11/1967   Knox et al.
(Continued)

FOREIGN PATENT DOCUMENTS

CN    202962945 U    6/2013
GB      2503275 A   12/2013
(Continued)

OTHER PUBLICATIONS

International Search Report and Written Opinion. PCT/NZ2015/000005. dated Apr. 22, 2015; pp. 9.
(Continued)

*Primary Examiner* — Nathan R Price
*Assistant Examiner* — Anh Bui
(74) *Attorney, Agent, or Firm* — Troutman Sanders LLP; John A. Morrissett; Scott A. Bergeson

(57) ABSTRACT

Described herein is a dispenser for dispensing fluid that, integrated into one hand piece, comprises a variable volume chamber with a plunger disposed within the chamber and a chamber inlet and outlet. The inlet and outlet communicate directly with a common chamber volume and the plunger translates in a linear direction relative to the chamber along a common longitudinal axis to expel fluid from the chamber (expel stroke) and/or draw fluid into the chamber (drawing
(Continued)

stroke). The plunger is linked to a controller, a power source and a motor that drives translation movement of the plunger. The dispenser described herein offers a variety of advantages over the art including accurate dosing without the user having the manually regulate the dose amount—the amount to be dosed is related to the volume of fluid in the chamber which can be pre-set or varied automatically using sensors and controllers.

19 Claims, 5 Drawing Sheets

(30) Foreign Application Priority Data

Sep. 12, 2014 (NZ) .................................. 631519
Sep. 12, 2014 (NZ) .................................. 700830

(51) Int. Cl.
  *B05C 17/00* (2006.01)
  *B05C 17/01* (2006.01)
  *A61M 5/315* (2006.01)
  *A61M 39/22* (2006.01)
  *A61M 5/145* (2006.01)
  *A61M 5/20* (2006.01)

(52) U.S. Cl.
  CPC ............ *A61M 5/315* (2013.01); *A61M 39/22* (2013.01); *B05C 17/003* (2013.01); *B05C 17/0133* (2013.01); *A61J 2200/76* (2013.01); *A61M 5/20* (2013.01); *A61M 5/204* (2013.01); *A61M 2005/2006* (2013.01); *A61M 2005/31588* (2013.01); *A61M 2205/3561* (2013.01); *A61M 2205/3584* (2013.01); *A61M 2205/3592* (2013.01); *A61M 2205/505* (2013.01); *A61M 2230/005* (2013.01); *A61M 2250/00* (2013.01); *B05C 17/0103* (2013.01)

(56) References Cited

U.S. PATENT DOCUMENTS

| | | | |
|---|---|---|---|
| 3,526,225 A | 9/1970 | Isobe | |
| 5,269,762 A | 12/1993 | Armbruster et al. | |
| 5,480,381 A | 1/1996 | Weston | |
| 5,560,317 A | 10/1996 | Bunyan et al. | |
| 5,716,007 A | 2/1998 | Nottingham et al. | |
| 5,827,219 A | 10/1998 | Uber, III et al. | |
| 5,833,661 A | 11/1998 | Trapp et al. | |
| 5,928,197 A | 7/1999 | Niehoff | |
| 5,997,500 A | 12/1999 | Cook et al. | |
| 6,159,161 A | 12/2000 | Hodosh | |
| 6,221,045 B1 | 4/2001 | Duchon et al. | |
| 6,558,352 B1 | 5/2003 | Hogan | |
| 6,783,512 B2 | 8/2004 | Bunyan | |
| 6,858,020 B2 | 2/2005 | Rusnak | |
| 6,929,619 B2 | 8/2005 | Fago et al. | |
| 7,056,307 B2 | 6/2006 | Smith et al. | |
| 9,775,697 B2 * | 10/2017 | Buckley | B05C 17/0133 |
| 2002/0107501 A1 | 8/2002 | Smith et al. | |
| 2003/0043043 A1 | 3/2003 | Hogan | |
| 2003/0093033 A1 | 5/2003 | Bunyan | |
| 2004/0015123 A1 * | 1/2004 | Smith | A61D 7/00 |
| | | | 604/65 |
| 2005/0124968 A1 | 6/2005 | Mollhagen | |
| 2005/0171476 A1 * | 8/2005 | Judson | A61M 5/14566 |
| | | | 604/131 |
| 2006/0108180 A1 | 5/2006 | Grach et al. | |
| 2009/0018505 A1 | 1/2009 | Arguedas et al. | |
| 2011/0224613 A1 * | 9/2011 | D'Antonio | A61M 5/204 |
| | | | 604/131 |
| 2012/0022447 A1 * | 1/2012 | Oliver | A61M 5/3234 |
| | | | 604/110 |

FOREIGN PATENT DOCUMENTS

| | | |
|---|---|---|
| NZ | 224789 A | 10/1989 |
| NZ | 247457 A | 3/1996 |
| NZ | 509851 A | 2/2001 |
| NZ | 523949 A | 4/2003 |
| WO | 2014/107766 A1 | 7/2014 |

OTHER PUBLICATIONS

International Preliminary Report on Patentability. PCT/AU2014/000014. Date of Completion Jun. 2, 2015; pp. 6.

* cited by examiner

FLUID DISPENSER

CROSS-REFERENCE TO RELATED APPLICATIONS

This is a U.S. National Phase application under 35 U.S.C. § 371 of International Patent Application No. PCT/NZ2015/000005, filed on 27 Jan. 2015 and published as WO 2015/112027, and claims benefit of priority to New Zealand Patent Application No. NZ631439, filed 27 Jan. 2014, New Zealand Patent Application No. NZ628257, filed 4 Aug. 2014, New Zealand Patent Application No. NZ631519, filed 12 Sep. 2014, and New Zealand Patent Application No. NZ700830, filed 12 Sep. 2014. The entire contents of these applications are hereby incorporated by reference.

TECHNICAL FIELD

Described herein is a fluid dispenser. More specifically, a fluid dispenser is described that may be used to accurately measure and dispense a dose of fluid to a subject such as a medicament to an animal through using a variable volume chamber and dosing components to control the volume in the chamber.

BACKGROUND

It is known that from time to time farmers are required to treat animals with fluid medicament. The medicament can be applied to the animal in the form of a vaccine, oral drench or pour on supplied from a bottle, pack or container capable of treating multiple animals. In all cases an applicator is used to apply the medicament to the animal.

A problem with such applicators is hand strain and fatigue for the farmer. This is noticeable when treating large numbers of animals and when applying larger doses of medicament.

Another problem with such applicators is most medicaments are dosed on weight. When dosing a group of animals, the farmer will set the applicator to suit the heavier animals and dose all the animals with the same amount. This results in over dosing of many animals and wasting of medicament.

Another problem with such applicators is a second spurt caused when the fluid in the supply tube is stopped quickly and the valves in the dispenser are unable to shut off the fluid immediately resulting in a second small dose being delivered. Increasing the spring force in the valves fixes the problem however this makes the applicator too difficult to operate.

Another problem with such applicators is there is no electronic means to record the animal identity, medicament, dose size and date.

Powered applicators have been developed to overcome the problem of hand strain and fatigue however these applicators are bulky, have the pumps mounted away from the operator and either run on mains power or are powered by pneumatic air supply. Some examples of art applicators include the following provided by way of example only.

NZ247457 describes a gun dispenser with a motor and batteries in the hand piece. The gun described does not have a separate chamber inlet and outlet. The dispenser is designed to expel fluid and no motorised and automated refilling is described. In addition, the motor is offset below the outlet axis making the dispenser bulky, unbalanced and difficult to control/aim.

NZ509851 describes a drench gun that relies on varying the motor speed in order to alter the volume of fluid dispensed from the gun. There is no separate chamber on the hand piece and the device is very reliant on the controller and motor accuracy to ensure the correct volume of fluid is dispensed.

NZ523949 describes a non-powered drench gun which has a fluid chamber in front of the piston and a chamber behind the piston. The piston has a non-return valve such that forward movement of the piston expels fluid from the front chamber and at the same time draws fluid from the reservoir into the rear chamber. The return stroke of the piston transfers fluid from the rear chamber to the front chamber, the chambers both containing the working fluid requiring a plunger that divides the chambers and integrated non-return valve between the chambers.

US2002/0107501 describes a weight dependent, automatic filling dosage system. The system has a separate pump that fills the syringe with the desired dosage. The operator has to squeeze the syringe handle to administer the dose, so the operator is still doing most of the work leading to the potential of injury. In addition, having separate components means the system is more cumbersome and less mobile.

It should be appreciated that it may be useful to address one or more of the above disadvantages or at least provide the public with a useful choice.

Further aspects and advantages of the dispenser will become apparent from the ensuing description that is given by way of example only.

SUMMARY

Described herein is a fluid dispenser that may be used to accurately measure and dispense a dose of fluid to a subject such as a medicament to an animal through using a variable volume chamber and dosing components to control the volume in the chamber.

In a first aspect, there is provided a dispenser for dispensing fluid that, integrated into one hand piece, comprises:
 a variable volume chamber with a plunger disposed within the chamber and a chamber inlet and outlet, the inlet and outlet communicating directly with a common chamber volume, wherein the plunger translates in a linear direction relative to the chamber along a common longitudinal axis;
 a controller that is operatively linked to the plunger and chamber;
 a power source and a motor that drives translation movement of the plunger thereby causing a change in volume in the chamber;
 a trigger; and
when the trigger is actuated the plunger translates to expel fluid in the chamber (expel stroke) and/or draw fluid into the chamber (drawing stroke) with the controller controlling the volume expelled and/or drawn into the chamber by varying the plunger translation distance or direction or speed or by altering combinations of these variations, In a second aspect, there is provided a dispenser for dispensing fluid that, integrated into one hand piece, comprises:
 a variable volume chamber with a plunger disposed within the chamber, wherein the plunger translates in a linear direction relative to the chamber along a common longitudinal axis, the plunger acting to:
  (a) draw a volume of fluid into the chamber (drawing stroke) via a chamber inlet in communication with the chamber;

(b) retain the drawn fluid volume inside the chamber; and
(c) expel fluid from the chamber (expel stroke) via a chamber outlet, the outlet being in communication with the chamber and wherein the outlet conveys fluid via an at least partly different pathway to the chamber inlet and wherein the inlet and outlet communicate with the same chamber volume and wherein the plunger position along the longitudinal axis is adjusted to vary the volume of fluid expelled from the chamber during the expel stroke;

a power source and a motor that drives translation movement of the plunger thereby causing a change in volume in the chamber resulting in drawing or expelling fluid stroke into or from the chamber;

a trigger, that when activated, causes fluid to be expelled from the chamber outlet; and, a hand piece casing that:
(i) at least partly encloses within the casing the power source, motor, and trigger; and,
(ii) retains the chamber, plunger, and chamber inlet and outlet integral to the hand piece.

In a third aspect, there is provided a dispenser for dispensing fluid that, integrated into one hand piece, comprises:
a variable volume chamber with a plunger disposed within the chamber and a chamber inlet and outlet, the inlet and outlet communicating directly with a common chamber volume, wherein the plunger translates in a linear direction relative to the chamber along a common longitudinal axis;
a controller that is operatively linked to the plunger and chamber;
a power source and a motor that drives translation movement of the plunger thereby causing a change in volume in the chamber;
a trigger; and
when the trigger is actuated the plunger translates to expel fluid in the chamber (expel stroke) and/or draw fluid into the chamber (drawing stroke) with the controller controlling the volume expelled from the chamber by adjusting the plunger position along the longitudinal axis during an expel stroke to vary the volume of fluid expelled from the chamber.

In a fourth aspect, there is provided a dispenser for dispensing fluid that, integrated into one hand piece, comprises:
a variable volume chamber with a plunger disposed within the chamber and a chamber inlet and outlet, the inlet and outlet communicating directly with a common chamber volume, wherein the plunger translates in a linear direction relative to the chamber along a common longitudinal axis;
a controller that is operatively linked to the plunger and chamber;
a power source and a motor that drives translation movement of the plunger thereby causing a change in volume in the chamber;
a trigger; and
when the trigger is actuated the plunger translates to expel fluid in the chamber (expel stroke) and/or draw fluid into the chamber (drawing stroke) with the controller varying the plunger translation distance based on the weight of a subject to which the fluid is to be applied thereby controlling the volume of fluid expelled and/or drawn into the chamber.

In a fifth aspect, there is provided a dispenser for dispensing fluid that, integrated into one hand piece, comprises:
a variable volume chamber with a plunger disposed within the chamber, wherein the plunger translates in a linear direction relative to the chamber along a common longitudinal axis, the plunger acting to:
(a) draw a volume of fluid into the chamber (drawing stroke) via a chamber inlet in communication with the chamber;
(b) retain the drawn fluid volume inside the chamber; and
(c) expel fluid from the chamber (expel stroke) via a chamber outlet, the outlet being in communication with the chamber and wherein the outlet conveys fluid via an at least partly different pathway to the chamber inlet; and
wherein the inlet and outlet communicate with the same chamber volume; and
wherein the plunger position along the longitudinal axis is adjusted to vary the volume of fluid expelled from the chamber during the expel stroke;

a power source and a motor that drives translation movement of the plunger thereby causing a change in volume in the chamber resulting in drawing or expelling fluid into or from the chamber;

a trigger, that when activated, causes fluid to be expelled from the chamber outlet; and, a hand piece casing that:
(i) at least partly encloses within the casing the power source, motor, and trigger; and,
(ii) retains the chamber, plunger, and chamber inlet and outlet integral to the hand piece.

In a sixth aspect, there is provided a dispenser for dispensing fluid that, integrated into one hand piece, comprises:
a variable volume chamber with a plunger disposed within the chamber, wherein the plunger translates in a linear direction relative to the chamber along a common longitudinal axis, the plunger acting to:
(a) draw a volume of fluid into the chamber (drawing stroke) via a chamber inlet in communication with the chamber;
(b) retain the drawn fluid volume inside the chamber; and
(c) expel fluid from the chamber (expel stroke) via a chamber outlet, the outlet being in communication with the chamber and wherein the outlet conveys fluid via an at least partly different pathway to the chamber inlet; and
wherein the inlet and outlet communicate with the same chamber volume; and
wherein the volume of fluid drawn or expelled into or from the chamber during the drawing or expel stroke is based on the weight of a subject to which the fluid is to be applied;

a power source and a motor that drives translation movement of the plunger thereby causing a change in volume in the chamber resulting in drawing or expelling fluid into or from the chamber;

a trigger, that when activated, causes fluid to be expelled from the chamber outlet; and, a hand piece casing that:
(i) at least partly encloses within the casing the power source, motor, and trigger; and,
(ii) retains the chamber, plunger, and chamber inlet and outlet integral to the hand piece.

In a seventh aspect, there is provided a dispenser for dispensing fluid that, integrated into one hand piece, comprises:
a variable volume chamber with a plunger disposed within the chamber and a chamber inlet and outlet, the inlet and outlet communicating directly with a common chamber volume, wherein the plunger translates in a linear direction relative to the chamber along a common longitudinal axis;

a controller that is operatively linked to the plunger and chamber;

a power source and a motor that drives translation movement of the plunger via a threaded shaft, the threaded shaft being approximately in-line with the chamber longitudinal axis of the motor thereby causing a change in volume in the chamber;

a trigger; and when the trigger is actuated the plunger translates to expel fluid in the chamber (expel stroke) and/or draw fluid into the chamber (drawing stroke) with the controller controlling the volume expelled and/or drawn into the chamber by varying the plunger translation distance or direction.

In a eighth aspect, there is provided a dispenser for dispensing fluid that, integrated into one hand piece, comprises:

a variable volume chamber with a plunger disposed within the chamber, wherein the plunger translates in a linear direction relative to the chamber along a common longitudinal axis, the plunger acting to:

(a) draw a volume of fluid into the chamber (drawing stroke) via a chamber inlet in communication with the chamber;

(b) retain the drawn fluid volume inside the chamber; and (c) expel fluid from the chamber (expel stroke) via a chamber outlet, the outlet being in communication with the chamber and wherein the outlet conveys fluid via an at least partly different pathway to the chamber inlet and wherein the inlet and outlet communicate with the same chamber volume;

a power source and a motor that drives translation movement of the plunger via a threaded shaft, the threaded shaft being approximately in-line with the chamber longitudinal axis, thereby causing a change in volume in the chamber resulting in drawing or expelling fluid into or from the chamber;

a trigger, that when activated, causes fluid to be expelled from the chamber outlet; and, a hand piece casing that:

(i) at least partly encloses within the casing the power source, motor, and trigger; and, (ii) retains the chamber, plunger, and chamber inlet and outlet integral to the hand piece.

In a ninth aspect, there is provided a method of dispensing a known dose of fluid to a non-human subject by the steps of:

(a) selecting a dispenser substantially as described above;

(b) at least partly filling the chamber with a volume of fluid; and (c) dispensing fluid to the non-human subject by activating the trigger.

The above dispensers and method offer a variety of advantages over the art including accurate dosing without the user having the manually regulate the dose amount—the amount to be dosed is related to the volume of fluid in the chamber which can be pre-set or varied automatically using sensors and controllers. Further advantages will become apparent from the detailed description below.

BRIEF DESCRIPTION OF THE DRAWINGS

Further aspects of the dispensers and method of use will become apparent from the following description that is given by way of example only and with reference to the accompanying drawings in which.

DETAILED DESCRIPTION

Figure 1:
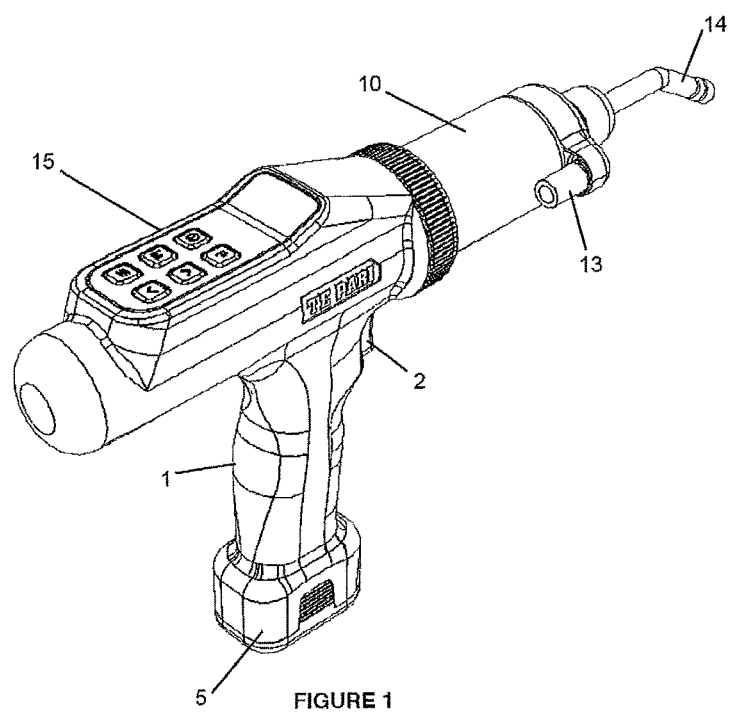
FIG. 1 illustrates a perspective view from above of a first embodiment of a dispenser.
Figure 2:
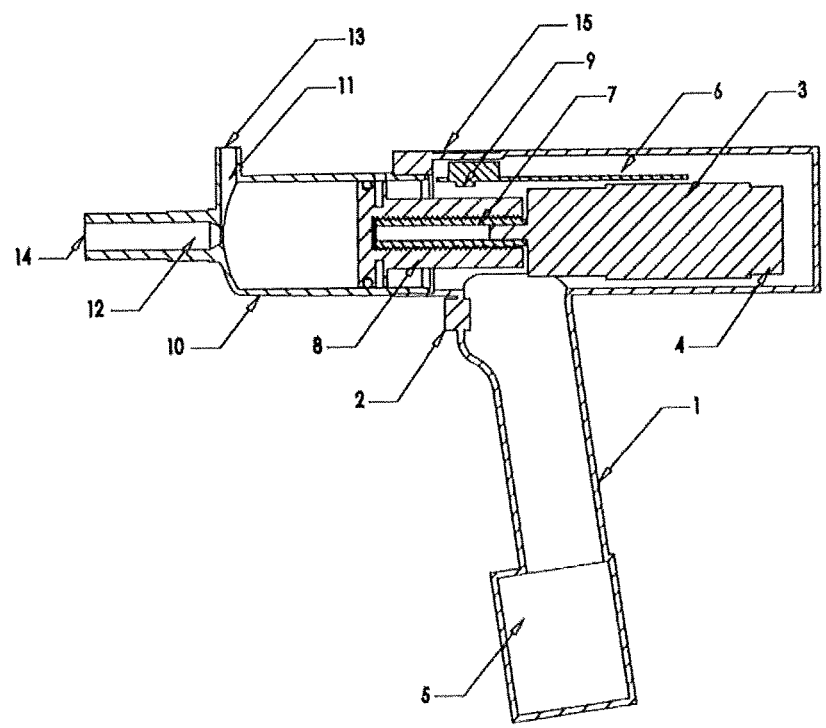
FIG. 2 illustrates a cross-section side view of a first embodiment of a dispenser.
Figure 3:
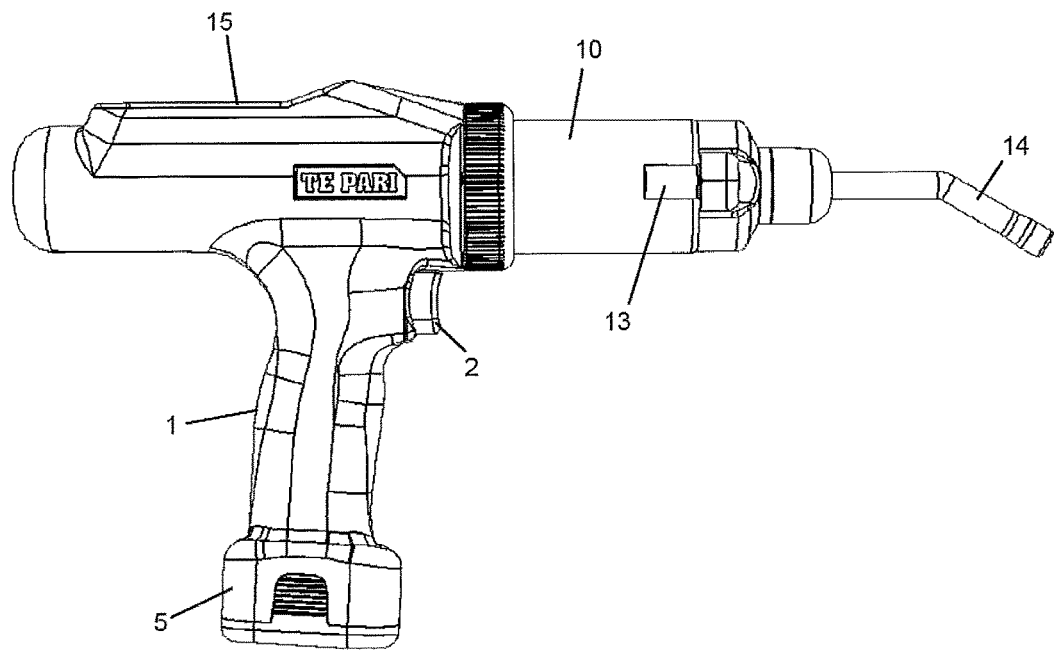
FIG. 3 illustrates an assembled side view of the above first embodiment of the dispenser.
Figure 4:
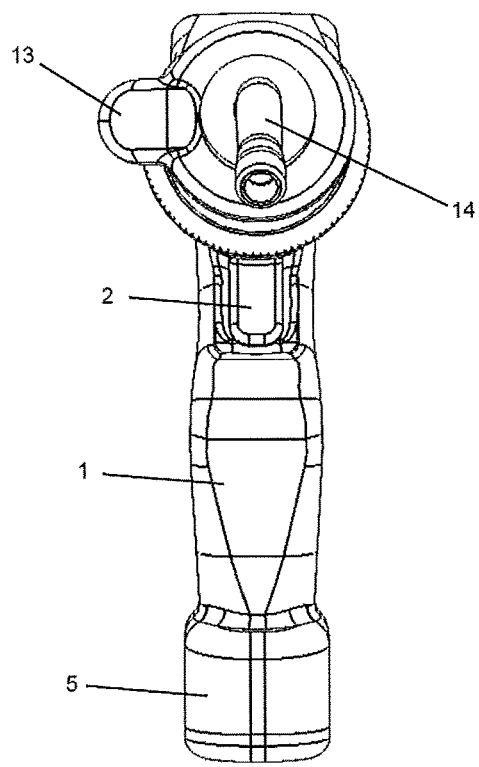
FIG. 4 illustrates an assembled front view of the above first embodiment of a dispenser.
Figure 5:
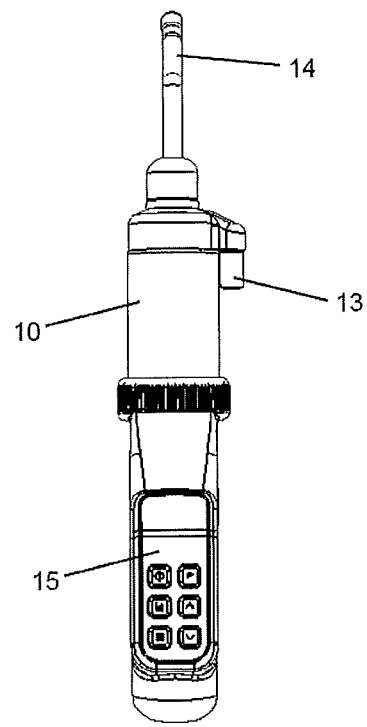
FIG. 5 illustrates top view of the above first embodiment of a dispenser.
Figure 6:
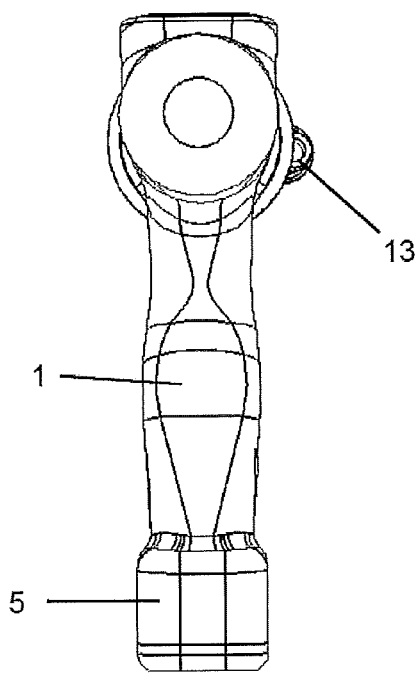
FIG. 6 illustrates rear view of the above first embodiment of a dispenser.
Figure 7:
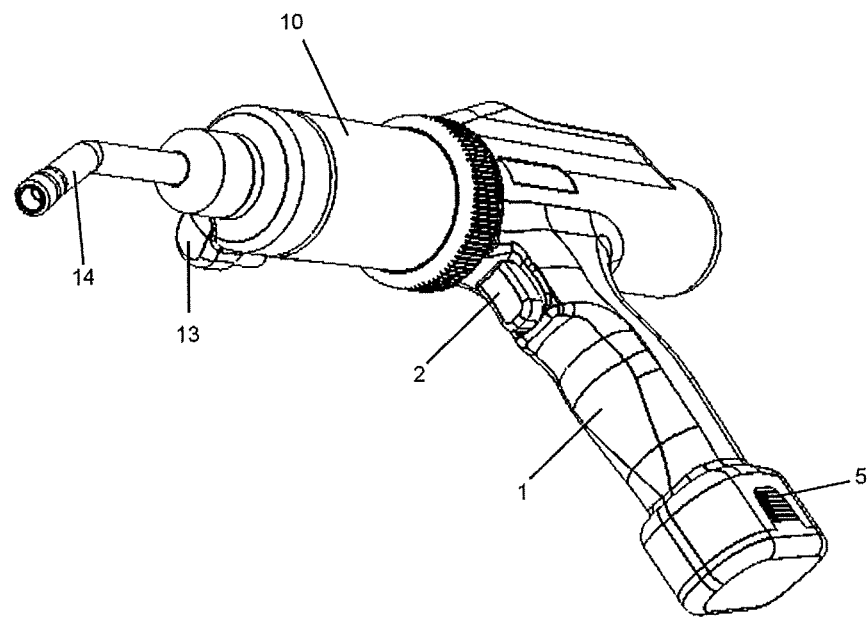
FIG. 7 illustrates a perspective view from below of the above first embodiment of a dispenser.

As noted above, described herein is a fluid dispenser that may be used to accurately measure and dispense a dose of fluid to a subject such as a medicament to an animal through using a variable volume chamber and dosing components to control the volume in the chamber.

For the purposes of this specification, the term 'about' or 'approximately' and grammatical variations thereof mean a quantity, level, degree, value, number, frequency, percentage, dimension, size, amount, weight or length that varies by as much as 30, 25, 20, 15, 10, 9, 8, 7, 6, 5, 4, 3, 2, or 1% to a reference quantity, level, degree, value, number, frequency, percentage, dimension, size, amount, weight or length.

The term 'substantially' or grammatical variations thereof refers to at least about 50%, for example 75%, 85%, 95% or 98%.

The term 'comprise' and grammatical variations thereof shall have an inclusive meaning—i.e. that it will be taken to mean an inclusion of not only the listed components it directly references, but also other non-specified components or elements.

The term 'fluid' or grammatical variations thereof refers to any gel to liquid viscosity semi-solid to liquid material. The fluid need not have Newtonian rheology and may have a variety of rheological properties. References made to the fluid being a medicament should not be seen as limiting as the dispenser assembly may be used to dispense non-medicament fluids.

The term 'subject' or grammatical variations thereof as used herein may be an animal or may instead be a substrate such as a plant or surface. References made to an animal should not be seen as limiting as it should be appreciated that the dispenser may be used to dispense fluid to any substrate.

The term 'hand piece' or grammatical variations thereof as used herein refers to an object of a dimension and shape to be held in one human hand and with a weight of approximately 10 kilograms or less.

In a first aspect, there is provided a dispenser for dispensing fluid that, integrated into one hand piece, comprises:

a variable volume chamber with a plunger disposed within the chamber and a chamber inlet and outlet, the inlet and outlet communicating directly with a common chamber volume, wherein the plunger translates in a linear direction relative to the chamber along a common longitudinal axis;

a controller that is operatively linked to the plunger and chamber;

a power source and a motor that drives translation movement of the plunger thereby causing a change in volume in the chamber;

a trigger; and when the trigger is actuated the plunger translates to expel fluid in the chamber (expel stroke) and/or draw fluid into the chamber (drawing stroke) with the controller controlling the volume expelled and/or drawn into the chamber by varying the plunger translation distance or direction or speed or by altering combinations of these variations, In a second aspect, there is provided a dispenser for dispensing fluid that, integrated into one hand piece, comprises:

a variable volume chamber with a plunger disposed within the chamber, wherein the plunger translates in a linear direction relative to the chamber along a common longitudinal axis, the plunger acting to:

(a) draw a volume of fluid into the chamber (drawing stroke) via a chamber inlet in communication with the chamber;

(b) retain the drawn fluid volume inside the chamber; and (c) expel fluid from the chamber (expel stroke) via a chamber outlet, the outlet being in communication with the chamber and wherein the outlet conveys fluid via an at least partly different pathway to the chamber inlet and wherein the inlet and outlet communicate with the same chamber volume and wherein the plunger position along the longitudinal axis is adjusted to vary the volume of fluid expelled from the chamber during the expel stroke;

a power source and a motor that drives translation movement of the plunger thereby causing a change in volume in the chamber resulting in drawing or expelling fluid stroke into or from the chamber;

a trigger, that when activated, causes fluid to be expelled from the chamber outlet; and, a hand piece casing that:

(i) at least partly encloses within the casing the power source, motor, and trigger; and, (ii) retains the chamber, plunger, and chamber inlet and outlet integral to the hand piece.

In a third aspect, there is provided a dispenser for dispensing fluid that, integrated into one hand piece, comprises:

a variable volume chamber with a plunger disposed within the chamber and a chamber inlet and outlet, the inlet and outlet communicating directly with a common chamber volume, wherein the plunger translates in a linear direction relative to the chamber along a common longitudinal axis;

a controller that is operatively linked to the plunger and chamber;

a power source and a motor that drives translation movement of the plunger thereby causing a change in volume in the chamber;

a trigger; and when the trigger is actuated the plunger translates to expel fluid in the chamber (expel stroke) and/or draw fluid into the chamber (drawing stroke) with the controller controlling the volume expelled from the chamber by adjusting the plunger position along the longitudinal axis during an expel stroke to vary the volume of fluid expelled from the chamber.

In a fourth aspect, there is provided a dispenser for dispensing fluid that, integrated into one hand piece, comprises:

a variable volume chamber with a plunger disposed within the chamber and a chamber inlet and outlet, the inlet and outlet communicating directly with a common chamber volume, wherein the plunger translates in a linear direction relative to the chamber along a common longitudinal axis;

a controller that is operatively linked to the plunger and chamber;

a power source and a motor that drives translation movement of the plunger thereby causing a change in volume in the chamber;

a trigger; and when the trigger is actuated the plunger translates to expel fluid in the chamber (expel stroke) and/or draw fluid into the chamber (drawing stroke) with the controller varying the plunger translation distance based on the weight of a subject to which the fluid is to be applied thereby controlling the volume of fluid expelled and/or drawn into the chamber.

In a fifth aspect, there is provided a dispenser for dispensing fluid that, integrated into one hand piece, comprises:

a variable volume chamber with a plunger disposed within the chamber, wherein the plunger translates in a linear direction relative to the chamber along a common longitudinal axis, the plunger acting to:

(a) draw a volume of fluid into the chamber (drawing stroke) via a chamber inlet in communication with the chamber;

(b) retain the drawn fluid volume inside the chamber; and (c) expel fluid from the chamber (expel stroke) via a chamber outlet, the outlet being in communication with the chamber and wherein the outlet conveys fluid via an at least partly different pathway to the chamber inlet; and wherein the inlet and outlet communicate with the same chamber volume; and wherein the plunger position along the longitudinal axis is adjusted to vary the volume of fluid expelled from the chamber during the expel stroke;

a power source and a motor that drives translation movement of the plunger thereby causing a change in volume in the chamber resulting in drawing or expelling fluid into or from the chamber;

a trigger, that when activated, causes fluid to be expelled from the chamber outlet; and, a hand piece casing that:

(i) at least partly encloses within the casing the power source, motor, and trigger; and, (ii) retains the chamber, plunger, and chamber inlet and outlet integral to the hand piece.

In a sixth aspect, there is provided a dispenser for dispensing fluid that, integrated into one hand piece, comprises:

a variable volume chamber with a plunger disposed within the chamber, wherein the plunger translates in a linear direction relative to the chamber along a common longitudinal axis, the plunger acting to:

(a) draw a volume of fluid into the chamber (drawing stroke) via a chamber inlet in communication with the chamber;

(b) retain the drawn fluid volume inside the chamber; and (c) expel fluid from the chamber (expel stroke) via a chamber outlet, the outlet being in communication with the chamber and wherein the outlet conveys fluid via an at least partly different pathway to the chamber inlet; and wherein the inlet and outlet communicate with the same chamber volume; and wherein the volume of fluid drawn or expelled into or from the chamber during the drawing or expel stroke is based on the weight of a subject to which the fluid is to be applied;
a power source and a motor that drives translation movement of the plunger thereby causing a change in volume in the chamber resulting in drawing or expelling fluid into or from the chamber;
a trigger, that when activated, causes fluid to be expelled from the chamber outlet; and,
a hand piece casing that:
(i) at least partly encloses within the casing the power source, motor, and trigger; and,
(ii) retains the chamber, plunger, and chamber inlet and outlet integral to the hand piece.

In a seventh aspect, there is provided a dispenser for dispensing fluid that, integrated into one hand piece, comprises:
a variable volume chamber with a plunger disposed within the chamber and a chamber inlet and outlet, the inlet and outlet communicating directly with a common chamber volume, wherein the plunger translates in a linear direction relative to the chamber along a common longitudinal axis;
a controller that is operatively linked to the plunger and chamber;
a power source and a motor that drives translation movement of the plunger via a threaded shaft, the threaded shaft being approximately in-line with the chamber longitudinal axis of the motor thereby causing a change in volume in the chamber;
a trigger; and
when the trigger is actuated the plunger translates to expel fluid in the chamber (expel stroke) and/or draw fluid into the chamber (drawing stroke) with the controller controlling the volume expelled and/or drawn into the chamber by varying the plunger translation distance or direction.

In a eighth aspect, there is provided a dispenser for dispensing fluid that, integrated into one hand piece, comprises:
a variable volume chamber with a plunger disposed within the chamber, wherein the plunger translates in a linear direction relative to the chamber along a common longitudinal axis, the plunger acting to:
(a) draw a volume of fluid into the chamber (drawing stroke) via a chamber inlet in communication with the chamber;
(b) retain the drawn fluid volume inside the chamber; and
(c) expel fluid from the chamber (expel stroke) via a chamber outlet, the outlet being in communication with the chamber and wherein the outlet conveys fluid via an at least partly different pathway to the chamber inlet and wherein the inlet and outlet communicate with the same chamber volume;
a power source and a motor that drives translation movement of the plunger via a threaded shaft, the threaded shaft being approximately in-line with the chamber longitudinal axis, thereby causing a change in volume in the chamber resulting in drawing or expelling fluid into or from the chamber;
a trigger, that when activated, causes fluid to be expelled from the chamber outlet; and,
a hand piece casing that:
(i) at least partly encloses within the casing the power source, motor, and trigger; and,
(ii) retains the chamber, plunger, and chamber inlet and outlet integral to the hand piece.

In a ninth aspect, there is provided a method of dispensing a known dose of fluid to a non-human subject by the steps of:
(a) selecting a dispenser substantially as described above;
(b) at least partly filling the chamber with a volume of fluid; and
(c) dispensing fluid to the non-human subject by activating the trigger.

The chamber, plunger and chamber inlet and outlet may be retained against the casing. The chamber, plunger and chamber inlet and outlet may be retained flush with the casing being held in a casing recess. Having the above items integral to a single hand piece may be useful to simplify design and operation and integrate all of the assembly into one hand held item. This however was not in the inventor's experience simple to achieve since careful placement and part selection was required to achieve the combined device in a lightweight form.

The chamber may have a substantially tubular shape and the plunger or a part thereof may sealingly engage with the interior wall of the chamber.

The volume between the chamber outlet and plunger head may define the dose size.

The hand piece may be a simple shape that can be held by a user in one hand and which has an outlet that for example, may be inserted directly into an animal mouth or which may be used to topically apply the fluid to an animal or substrate. The outlet may also be an injection needle.

The hand piece casing may:
(i) at least partly enclose within the casing the power source, motor, controller, and trigger; and,
(ii) retain the chamber, plunger, and chamber inlet and outlet integral to the hand piece.

The dispenser may be gun shaped with a grip portion and barrel portion that extends over the top of the grip portion, the grip including the power source and trigger, and wherein the barrel portion includes the chamber, fluid if present, at least part of the motor, and the plunger.

In one embodiment, the fluid outlet may be offset from a hand piece grip region by approximately 70 to 100 degrees. A gun shape typically has this alignment as a normal part of the design. Having the grip handle or trigger offset in this manner may provide for a more ergonomic design that is both aesthetically pleasing and minimises risk of injury through difficult positioning. In an alternative embodiment, the outlet or grip region of the hand piece may be adjustable in angle relative to the outlet allowing the user to manipulate the shape of the assembly to suit the method of administration and alignment of the substrate or subject relative to the user.

The chamber and parts therein may be off set or separate to the grip region of the hand piece. While it may be possible to have the user grip the chamber, it may be helpful to have the chamber mounted separately to the grip region so as to avoid the chamber being limited in size dependent on the users handgrip. Natural handgrips only extend up to a point dependent on the users hand size after which it becomes cumbersome and even impossible to hold a grip region comfortably and with precision.

The motor may be approximately in-line with the chamber longitudinal axis and located within or about the grip portion. The motor may be located wholly within the grip portion.

Plunger translation movement may be driven by the motor via a threaded shaft. The threaded shaft may be approximately in-line with the chamber longitudinal axis.

In one embodiment, the drive means may be a helical screw.

The threaded shaft may be approximately in-line with the chamber longitudinal axis with the motor. The drive thread may be oil filled nylon running in an acetal plunger. The pitch and type of thread may be important for efficiency. The drive thread may be mounted inline with the motor for efficiency—in the inventor's experience, offset motors may be used such as gear drives and belt drives but the drive efficiency may be reduced.

The plunger position may be along the longitudinal axis and may be adjusted to vary the volume of fluid drawn into the chamber during the drawing stroke.

The plunger position along the longitudinal axis may be adjusted to vary the volume of fluid expelled from the chamber during the expel stroke.

The volume of fluid expelled from the chamber during the expel stroke may be based on the weight of a subject to which the fluid is to be applied. As may be appreciated, use of weight to gauge dose size may be highly advantageous—most medicaments dose based on live weight. In art environments, the dose given is typically pre-set and not varied during a dosing run with the effect that the dose received may be excessive or insufficient. Both of these extremes are unfavourable for the animal and, if excessive, results in wasting of medicament, which can be expensive. Assessing weight of an animal either visually or via weighing apparatus such as scales and using that data to set the dose expelled eliminates the dose variation thereby avoiding art problems.

The weight data may be sent wirelessly to the at least one controller and the controller may set the volume in the chamber based on a dose rate of fluid required to suit the measured weight of the subject.

The subject to which fluid is to be dispensed may be weighed and the weight measured received by the at least one controller and used as an additional input to set the volume of fluid to be dispensed. The controller may set the volume in the chamber based on a dose rate of fluid required to suit the measured weight of the subject. This embodiment may be particularly advantageous as it allows the dispensing assembly to be used to accurately assess and dispense a dose appropriate to the weight, for example, of an animal to which the fluid, e.g. medicament, is to be dispensed. Correct dosing and automatic adjustment specific to each animal avoids over dosing and avoids wastage of medicament. The benefits of this include avoidance of animal health issues associated with an overdose plus this reduces medicament costs significantly.

The weight data may be measured on a scale or scales immediately prior to dispensing. In one embodiment, the weight information may be sent wirelessly to the at least one controller. Wireless transfer means are well known in the art for example via WiFi™, Bluetooth™ and cellular networks. An advantage of wireless transmission is the avoidance of extra cords or wires between the dispenser outlet and the weigh scale/s.

The chamber may be releasably attached to the hand piece. Releasable attachment allows for easy cleaning and/or replacement of the chamber and parts therein such as the plunger or plunger seal if used. This may be an advantage where a processing run is completed and the chamber and contents require cleaning and reassembly prior to further use or storage. This also may be important to increase the lifecycle of the dispenser allowing replacement and servicing of the main moving parts.

Actuation of the trigger may cause an expel stroke and, subsequently, a drawing stroke. Actuation of the trigger may alternatively cause an expel stroke and, when the trigger is released, a drawing stroke occurs. Fluid in the chamber may be expelled from the outlet in one action of the dispenser (e.g. forwards movement of the plunger reducing the fluid volume in the tube), and the chamber re-filled in a second action of the dispenser assembly (e.g. caused by reverse movement of the plunger in the tube creating a suction force that encourages fluid movement into the chamber void). In one embodiment, 'normal' operation involves the user pulling the trigger once to dispense a dose. Holding down the trigger makes no difference, the gun will only dispense a single dose until the trigger is released and pulled again. The dispenser may be switched to a so called 'prime mode' where, when the user pulls the trigger, the plunger moves and when the trigger is released, the plunger stops and then returns to the start position. This allows the user to fill an inlet supply tube and the chamber and then stop when the last of the air is expelled from the chamber. This saves wastage and also minimises the risk of contact with the fluid, important in handling some fluids. In one embodiment, in normal operation (not in prime mode) the chamber and inlet supply may be always at least partly full of fluid.

The chamber inlet may be located at or about one distal end of the chamber, and the chamber inlet is also located about, but separate to, the outlet. In this embodiment, the inlet and outlet may be located about the end of the chamber furthest from the grip portion of the dispenser. Both the inlet and outlet may be located close together but separated enough that fluid flows in different directions with respect to each part. The term 'mounted on the chamber' refers to the inlet and outlet being at least partly mounted integral to the chamber although for example, if the inlet and outlet are moulded tubes, there may be some overlap between the tubes, in this embodiment also having both tubes also at least partly moulded to the chamber. The inlet and outlet may be located perpendicular to each other about a common plane.

The chamber inlet may be linked to a fluid transport tube and the opposing end of the tube is linked to a fluid reservoir. The fluid reservoir may be a backpack or other receptacle that retains a bulk quantity of the fluid.

In one embodiment where the dispenser is gun shaped, the inlet tube runs along the gun barrel and may be secured to the gun casing. Securement of the tubing to the casing may be useful as, if not secured, the tube may get in the way of operation of the dispenser or may snag or items in the dispenser working area, pulling the tube off the inlet potentially resulting in spilt fluid. In the inventor's experience, other art dispensing devices do not secure inlet tubing (if used) to the dispenser.

The inlet and outlet may include a valve or valves to prevent egress of fluid from the chamber prior to dispensing. The valve may be a one-way valve that in the case of the inlet allows fluid to enter the chamber but not exit the chamber and in the case of the outlet, the valve may only allow fluid to escape but not enter the chamber. The valve or valves may only allow fluid movement there through when subjected to a force sufficient to break the valve seal.

The dispenser may include a controller to measure and determine a volume of fluid in the chamber. The dispenser may include a controller to measure and determine a volume of fluid drawn into and/or expelled from the chamber. The controller, during an expel stroke or drawing stroke, may vary at least one aspect of the dispenser action selected from:

motor direction, plunger stroke speed, duration of movement, and combinations thereof. In one embodiment, the motor speed may vary to slow the rate of dispensing during a dispensing action. In one embodiment, the dose speed may be reduced towards the end of the dispensing action to prevent the after spurt that may occur in art applicators. The speed of dispensing may also be controlled slow or fast or varying for example to allow the animal time to swallow the fluid where the fluid is an oral drench. Too rapid dispensing may result in the animal simply expelling the fluid from their mouth.

The dispenser may include at least one sensor that measures the plunger position relative to the tube. As may be appreciated, it is important to make the device or device processer 'aware' of the initial plunger position assuming a plunger is used. This initial position may equate to a first fully retracted and maximum fluid holding volume in the chamber or tube and sets a datum or reference point. The initial and/or secondary measured position may be a fully deployed plunger position and minimal fluid holding volume position. Intermediate datum positions may also be used as a frame of reference. The sensor may read an external signal from the chamber walls, one example being an electrical signal about a wall point or region. Another example may be to use a physical stop that acts as a reference point. A further example may be a magnet or magnets that interact with a plunger at a point or region of the chamber.

The controller may be used to determine where the plunger home/start position is. This can be factory set however if the power source is disconnected mid stroke the controller may not be able to return the plunger to the home position. It may be possible for the controller to record where the plunger is when the power stops however sometimes this may not be reliable. Various means to detect and control plunger position and therefore cause accurate and repeatable dispensing are described below.

The controller may measure plunger momentum by counting motor revolutions past a theoretical stop point during a stroke step and then compensates for this in the next stroke, so after one or two strokes the controller has calibrated the plunger movement thereby avoiding any variance in volume caused by plunger momentum.

As noted above, the drive mechanism may have a momentum effect that can impact on the plunger position and contribute to drift an eventual wrong positioning of the plunger. As noted above, the controller may measure the momentum by counting motor revolutions past the theoretical stop point and then compensate for this in the next stroke. After one or two strokes the controller may have calibrated the plunger to allow for any momentum drift. Momentum may vary depending on fluid viscosity and ambient temperature.

In one embodiment, the motor rotates when a plunger stroke occurs. The sensor or sensors may measure the number of revolutions completed by the motor, a set number of rotations correlating to a known and measurable change in fluid void space within the chamber or tube.

The dispenser may further include at least one sensor that measures the motor current, wherein motor current changes as the volume in the chamber changes. In one embodiment, the current changes when a physical stop is struck by the plunger, the restriction in movement resulting in a variation in motor current.

The dispenser may include at least one sensor that measures the time between encoder pulses from the motor, wherein the time between encoder pulses changes when the volume reaches a pre-determined size.

A magnet and magnet sensor may be incorporated into the dispenser such that, when in communication, the controller receives a signal indicating a specific translation position of the plunger with respect to the chamber.

The use of a magnet may be as a back up check. On power up of the dispenser, if the sensor does not register the magnet it will reverse the plunger until the magnet is sensed thereby calibrating the plunger position.

As should be appreciated a combination of the above sensor options may be used to correctly measure and set the plunger position as well as recalculate and measure the plunger position during and after each stroke or strokes. One scenario of where a combination of sensors may be useful is to allow one or more controller to compensate for any wear or slippage in the plunger position caused by variations in a drive means between the motor and plunger.

The dispenser may include one or more controllers that receive data collected from one or more sensors and, based on the data received, adjust the plunger position to set the volume of fluid in the chamber. The controller may for example, know a desired and pre-determined volume of fluid that needs to be dispensed and after each dispensing action, the controller re-calculates the desired position of the plunger in order to draw up the desired dose volume and the controller or controllers instruct the physical volume changes. The controller or controllers may include one or more processors or micro-processors.

In one embodiment, the dispenser electronic parts, motor and power source may be manufactured to have a waterproof coating. The hand piece casing may be waterproof. In certain applications of use of the dispenser, the working environment may be dirty and wet hence, ideally the dispenser prevents dirt and moisture ingress. Also the hand piece assembly should allow the user to be able to clean the dispenser using water or a water soaked cloth.

Ideally the electronics, motor and batteries require waterproofing. In one embodiment, the hand piece may be fully sealed with the electronics, motor and batteries mounted inside with either a vent hole or means to flex or an expansion chamber to allow the plunger to move freely. Alternatively the electronics, motor and batteries could be individually sealed and mounted in an unsealed hand piece. Alternatively it could be a combination of the sealing options. Further, as noted above, the parts are mounted integral as a single hand piece and the hand piece casing may also be at least shower proof or water resistant on at least the top and sides.

The hand piece casing and/or chamber may include at least one air vent.

As the inventor's realised during development of the dispenser, the case and/or chamber may require air venting. This is useful in order to drain any water that manages to enter the casing. A vent or vents may also be important to provide air movement for the plunger as if, fully sealed, the motor will need to work harder and/or the assembly will need to flex in order to allow for plunger movement—this is particularly the case where the plunger forms a tight seal with the interior walls of the chamber. The at least one air vent could be in the hand piece or barrel or anywhere behind the plunger head/seal.

In one embodiment, when the plunger translates during an expel stroke, fluid is expelled in front of the plunger or part thereof, and a corresponding volume of air may be drawn into the chamber behind the plunger.

In one embodiment, the chamber may be sealed and when the plunger moves it pumps up to 5, or 10, or 15, or 20, or 25, or 30, or 35, or 40, or 45, or 50, or 55, or 60, or 65, or 70, or 75, or 80, or 85, or 90, or 95, or 100 ml of fluid in front of the plunger head and a corresponding 5, or 10, or 15, or 20, or 25, or 30, or 35, or 40, or 45, or 50, or 55, or 60, or 65, or 70, or 75, or 80, or 85, or 90, or 95, or 100 ml of air is drawn into the chamber behind the plunger head.

The air vent noted above in the hand piece casing or chamber may be at a point located behind the plunger or part thereof.

Optionally, a membrane may be used to stop water ingress but still allow air movement. Any water leaks into the case may be managed and directed via a gutter or gutters directing the water to the vent. Should the motor require cooling vents then these could also act as the plunger vent.

The fluid used in the dispensers and method may be a pour on medicament, an oral drench medicament, or an injectable medicament and the subject may be a non-human animal. The dispensing assembly may be particularly useful in animal health work where such devices can minimise labour, avoid injuries and speed processing through more effective design. This example of use should not however be seen as limiting since the dispenser could be used for a wide range of fluids and substrates to which the fluid is applied.

The subject to which fluid is to be dispensed may be weighed and the weight measured received by at least one controller and used to set the volume of fluid to be dispensed.

In the above embodiments, fluid present in the chamber may be visible to a user of the assembly. This may be useful to allow the user to quickly see via a visual check, the presence of fluid in the chamber and even the plunger position to ensure correct operation.

The dispenser may include an interface. The interface may be one or more displays. The displays may be controlled via touch screen and/or controlled via one or more buttons or switches. The interface or display may allow the operator to change aspects of the dispensing assembly tuning and performance. Aspects of the fluid dynamics and characteristics may also be entered into the controller such as dose to weight ratios.

The power source may be a DC power supply. In one embodiment, the power source may be at least one battery. The power source may alternatively be a mains power source with or without a DC converter.

The motor may be a standard DC motor that is supplied with an encoder and a planetary gearbox. The inventors tested stepper motors and brushless motors. Stepper motors have accurate control but run hot, well over 60 deg C. at times. Brushless motors are still too expensive. Motor temperature is an issue because the gun needs to be waterproof and venting is difficult. A DC motor may be useful as it runs cool enough to be plastic wrapped and not vented.

The batteries may be lithium 18650 cells that in the inventor's experience may last for about 2000 40 ml volume doses. NiMH batteries could also be used to run the pump but for fewer strokes—in the inventor's experience, approximately 1000 40 ml volume doses. Batteries may be ideal in some applications such as in on farm drenching applications, as there is no need to run cables from the hand piece to a power source such as an AC source. For drenching, farmers typically either hold individual animals in a crush or line animals up in a race and either walk down the side of the race or through the race dosing animals. Mobility in this embodiment is essential. There are systems available that run off compressed air or LPG but they require carrying a tank in a backpack along with the drench. The LPG gives operators headaches and is environmentally damaging. The dispenser design described herein allows the farmer improved portability.

Varying outlet types may be used to suit the desired fluid and method of dispensing. For example, if the fluid is formulated for injection, the outlet may be a needle. If the fluid is formulated for oral delivery, the outlet may be a mouth acceptable size and shape. In one embodiment, the chamber outlet may be a spot or spray nozzle. Spot or spray nozzles may be useful if the fluid is formulated for topical administration and/or administration to a substrate.

The above dispensers and method offer a variety of advantages over the art including accurate dosing without the user having the manually regulate the dose amount—the amount to be dosed is related to the volume of fluid in the chamber which can be pre-set or varied automatically using sensors and controllers. The metered dose is calculable and repeatable. Further, since the amount dispensed is based on fluid volume, different rheology and viscosity fluids may be accurately and repeatedly dispensed from the dispensing assembly. Art devices often rely on knowing the fluid viscosity to ensure accurate dispensing since the amount dispensed relies on a hand trigger with a greater pull resulting in a greater amount of fluid being dispensed. High viscosity hampers trigger pull in art devices since the fluid dispensed correlates to user strength and not a pre-determined and motorised volume.

The embodiments described above may also be said broadly to consist in the parts, elements and features referred to or indicated in the specification of the application, individually or collectively, and any or all combinations of any two or more said parts, elements or features, and where specific integers are mentioned herein which have known equivalents in the art to which the embodiments relates, such known equivalents are deemed to be incorporated herein as of individually set forth.

Where specific integers are mentioned herein which have known equivalents in the art to which this invention relates, such known equivalents are deemed to be incorporated herein as if individually set forth.

WORKING EXAMPLES

The above described dispenser and method of use are now described by reference to specific examples.

Example 1

As shown in FIGS. 1 to 7, one embodiment of the dispenser may be a hand piece in the shape of a gun. The gun comprises a hand piece 1 fixed to a tube 10, battery pack 5, trigger 2, motor 3, preferred encoder 4, a fluid inlet 13, a fluid outlet 14, drive means 7 and 8 wherein drive means 7 is a threaded rod attached to a motor shaft and drive means 8 is a plunger that threads over drive means 7 and is keyed to a non-rotating part to stop the plunger 8 rotating such that rotating drive means 7 a determined number of revolutions causes the plunger 8 to move a calculated distance relative to tube 10 such distance based on the pitch of drive means 7 resulting in a calculated amount of fluid in tube 10 being dispensed from outlet 14 and in a second action rotating drive means 7 a determined number of revolutions causes the plunger 8 to move a calculated distance relative to tube 10 resulting in a calculated amount of fluid from inlet 13 being refilled into tube 10, a controller 6, an interface 15, a sensor 9, inlet valve 11 positioned between the tube 10 and the fluid inlet 13, an outlet valve 12 positioned between the tube 10 and outlet 14. A sensor 9 in communication with controller 6 is mounted to detect the linear axial position of plunger 8 relative to tube 10 such that the controller 6 can allow for any wear or slippage in the drive means, plunger, motor or encoder.

As may be appreciated, the above dispenser may be used in a manual mode where the user sets the dose size. Alternatively, the dispenser may be used in an automatic mode where the dose size is automatically set by the weight of the animal or some other item of data.

Example 2

As noted in the above description in FIG. 1, all parts of the dispenser may be integrated into one unit, the only external items being a sensor of sensors that send information to the dispenser such as animal weight and the medicament itself (which is drawn into the dispenser chamber via a tube (not shown).

As should be appreciated, other configurations may also be used. In this example, the dispenser (not shown) comprises a gun portion mounted on the belt of the user and an extension hand held outlet is held in the user's hand. The trigger may be mounted on the gun and/or on the extension hand held outlet.

Example 3

In this example a further configuration is described whereby some or all of the dispenser parts are mounted to animal handling equipment e.g. a cattle or sheep crush unit. The parts may be mechanized to dose the animal absent of the user being directly present.

Example 4

Figure 8:
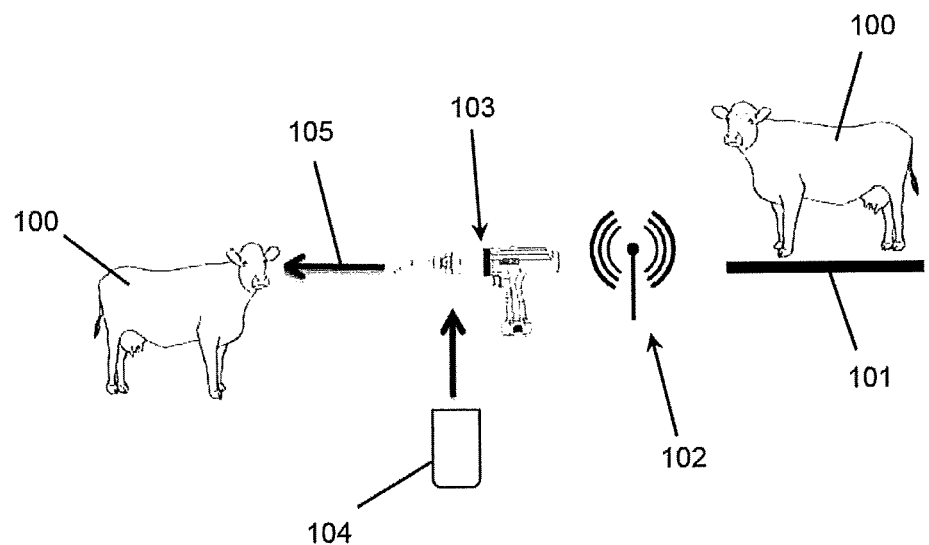
FIG. 8 illustrates a diagram of an embodiment of dispenser information flow.
Figure 9:
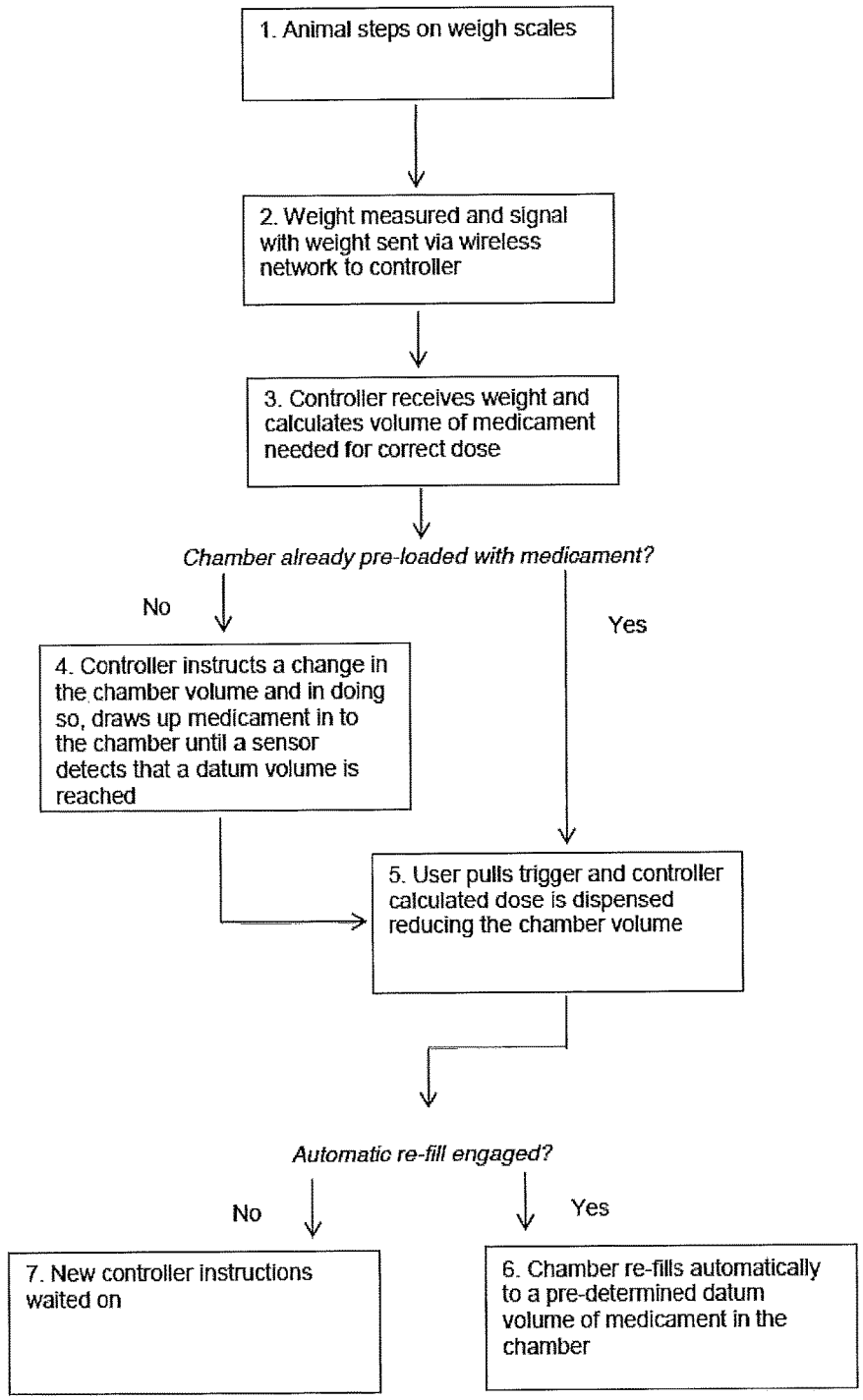
FIG. 9 illustrates a flow diagram of one method of use of the dispenser.

Referring to FIGS. 8 and 9, the method of use and actions taken in an automated dispensing operation are shown.

Note that in FIG. 8, a cow is shown but the dispenser may be used with other animals or other items. The cow 100 steps onto a weighing platform 101 and the weighing platform measures the cow 100 weight via a sensor (not shown). The measured weight is sent as a signal via a wireless network 102 to a controller mounted in or on the dispenser 103, in this case illustrated as the gun embodiment of Example 1. As should be appreciated, the dispenser may take other forms as noted in Examples 2 and 3 above.

The controller then calculates the required dose of medicament. If the chamber already includes a pre-set amount of medicament, dispensing can continue when the user activates the trigger. Alternatively, if the chamber is empty or requires more medicament, the controller may draw up this dose (or additional dose) from a storage container 104. When the user activates the trigger, the dispenser then dispenses the pre-determined amount 105.

Depending on design choice, the chamber may then automatically refill in part or fully so that it is pre-loaded for the next dose. Alternatively, the dispenser may await a further instruction before the chamber is re-filled, one example being a new animal weight and subsequent dose calculation.

Aspects of the dispensers and method have been described by way of example only and it should be appreciated that modifications and additions may be made thereto without departing from the scope of the claims herein.

The invention claimed is:

1. A dispenser for dispensing fluid comprising:
   a variable volume chamber with a plunger disposed within the chamber;
   a motor configured to drive translation movement of the plunger to cause a change in volume in the chamber;
   a trigger; and
   a controller in communication with the motor and the trigger, the controller being configured to:
   receive a first variable input based on a first subject to which fluid is to be applied;
   receive a second variable input based on a second subject to which fluid is to be applied;
   in response to actuation of the trigger, direct the motor to drive translation movement of the plunger to one or more of expel fluid from the chamber (expel stroke) and draw fluid into the chamber (draw stroke);
   automatically control the volume of fluid expelled from the chamber during a first expel stroke based on the first variable input such that only a first volume of fluid is expelled from the chamber, the first volume of fluid being less than an entire volume of fluid in the chamber;
   following the first expel stroke, cause a first draw stroke to occur, the fluid drawn into the chamber during the first draw stroke having the same volume as the first volume of fluid; and
   following the first draw stroke, automatically control the volume of fluid expelled from the chamber during a second expel stroke based on the second variable input such that only a second volume of fluid is expelled from the chamber, the second volume of fluid being less than the entire volume of fluid in the chamber.

2. The dispenser of claim 1, wherein the first and second variable inputs comprise a measured weight of the first and second subjects, respectively, and the controller being further configured to automatically control a plunger translation distance for the first and second expel strokes based on the measured weights of the first and second subjects, respectively.

3. The dispenser of claim 1, further comprising a power source configured to power the motor, and a hand piece casing that is configured to:
   at least partly enclose the power source, the motor, the controller, and the trigger; and
   hold the chamber and the plunger integral to the hand piece.

4. The dispenser of claim 1, further comprising a chamber inlet and outlet communicating directly with a common chamber volume, wherein the chamber inlet is positioned proximate to a distal end of the chamber, and the chamber inlet being positioned about, but separate from, the chamber outlet.

5. The dispenser of claim 3, wherein the hand piece casing is gun shaped and forms a grip portion and a barrel portion that extends over a top of the grip portion, the grip portion housing the power source and the trigger, and the barrel portion housing the chamber, at least a portion of the motor, and the plunger.

6. The dispenser of claim 5, wherein the motor is positioned approximately in-line with a longitudinal axis of the chamber and disposed within or about the grip portion.

7. The dispenser of claim 5, wherein:
   the motor is configured to drive translation movement of the plunger via a threaded shaft to cause the first draw stroke to occur by drawing fluid into the chamber, the threaded shaft being positioned approximately in-line with a longitudinal axis of the chamber, the first volume of fluid is expelled from the chamber by directing the threaded shaft to rotate a first predetermined number of revolutions based on the first variable input to adjust a position of the plunger along the longitudinal axis, and the second volume of fluid is expelled from the chamber by directing the threaded shaft to rotate a second predetermined number of revolutions based on the second variable input to adjust the position of the plunger along the longitudinal axis.

8. The dispenser of claim 1, wherein the controller is further configured to, during a stroke, vary at least one of a motor direction, a plunger stroke speed, and a duration of movement.

9. The dispenser of claim 8, wherein the controller is further configured to measure a momentum of the plunger by counting motor revolutions past a theoretical stop point during a stroke, and compensate for the measured momentum in a subsequent stroke to calibrate the plunger.

10. The dispenser of claim 8, further comprising a magnet and a magnet sensor in communication with the controller, the controller being further configured to receive, from the magnet sensor, a signal indicating a specific translation position of the plunger with respect to the chamber.

11. The dispenser of claim 3, wherein one or more of the hand piece casing and the chamber comprises at least one air vent, the at least one air vent being configured to draw a corresponding volume of air into the chamber behind the plunger when the plunger translates during an expel stroke.

12. The dispenser of claim 11, wherein the air vent is positioned behind at least a portion of the plunger.

13. The dispenser of claim 1, wherein the controller is further configured to automatically control the volume expelled from the chamber by varying one or more of a plunger translation distance and a translation direction based on the at least one variable input.

14. A dispenser for dispensing fluid comprising:
a variable volume chamber with a plunger disposed within the chamber;
a motor configured to drive translation movement of the plunger thereby causing a change in volume in the chamber;
a trigger;
a controller in communication with the motor, and the trigger, the controller being configured to:
receive at least one variable input based on a subject to which the fluid is to be applied;
automatically adjust a position of the plunger based on the at least one variable input to control the volume of fluid expelled from the chamber during an expel stroke;
in response to the activation of the trigger, direct the motor to drive translation movement of the plunger to cause less than the entire volume of fluid to be expelled from the chamber; and
following the expel stroke, direct the motor to drive translation movement of the plunger to draw fluid into the chamber, the fluid drawn into the chamber having the same volume as the less than the entire volume of fluid expelled from the chamber in the preceding expel stroke.

15. The dispenser of claim 14, wherein the controller is further configured to:
receive a measured weight of the subject; and
automatically adjust the volume of fluid within the chamber based on the measured weight of the subject.

16. The dispenser of claim 14 further comprising a chamber inlet and outlet, wherein:
the inlet and outlet communicate with the same chamber volume;
the motor is configured to drive translation movement of the plunger via a threaded shaft, the threaded shaft being approximately in-line with the longitudinal axis of the chamber, thereby causing a change in volume in the chamber resulting in drawing or expelling fluid into or from the chamber; and
the controller is further configured to, in response to activation of the trigger, automatically expel fluid from the chamber outlet.

17. The dispenser of claim 14, wherein the at least one variable input comprises a measured weight of the subject, the controller being further configured to control the volume of fluid expelled from the chamber during each expel stroke based on the measured weight of the subject.

18. The dispenser of claim 14, wherein causing less than the entire volume of fluid to be expelled from the chamber results in a first volume of fluid being expelled from the chamber and a second volume of fluid remaining in the chamber.

19. The dispenser of claim 14, wherein the volume of fluid expelled from the chamber during the expel stroke may be automatically varied by driving translation movement of the plunger to a different end position than an end position of a previous expel stroke, wherein the plunger position of the expel stroke and the previous expel stroke begin at the same starting position within the chamber.

* * * * *